United States Patent
Chou et al.

(10) Patent No.: US 7,598,546 B1
(45) Date of Patent: Oct. 6, 2009

(54) SEPARATIVE EXTENDED GATE FIELD EFFECT TRANSISTOR BASED VITAMIN C SENSOR AND FORMING METHOD THEREOF

(75) Inventors: Jung-Chuan Chou, Yunlin County (TW); E-Ling Huang, Tainan (TW); Chang-Chi Lee, Yunlin County (TW); Chien-Cheng Chen, Taichung County (TW)

(73) Assignee: National Yunlin University of Science and Technology, Yunlin (TW)

( * ) Notice: Subject to any disclaimer, the term of this patent is extended or adjusted under 35 U.S.C. 154(b) by 0 days.

(21) Appl. No.: 12/344,427

(22) Filed: Dec. 26, 2008

(30) Foreign Application Priority Data

Jun. 30, 2008 (TW) .............................. 97124536 A (51) Int. Cl.
*H01L 21/336* (2006.01)
*H01L 29/78* (2006.01)

(52) U.S. Cl. ............... 257/253; 257/414; 257/E29.325; 257/E21.401; 438/49

(58) Field of Classification Search ................. 257/253, 257/414, E21.401, E29.325; 438/49
See application file for complete search history.

(56) References Cited

U.S. PATENT DOCUMENTS

2002/0132226 A1* 9/2002 Nair et al. ...................... 435/4
2007/0095664 A1* 5/2007 Chou et al. ................. 204/433

FOREIGN PATENT DOCUMENTS

TW 2008/04803 A * 1/2008
WO WO 2005/034204 A2 * 4/2005

* cited by examiner

*Primary Examiner*—Evan Pert
(74) *Attorney, Agent, or Firm*—Quintero Law Office (57) ABSTRACT

A separative extended gate field effect transistor based vitamin C sensor includes: a substrate; a patterned conductive layer on the substrate, including a first electrode region array, at least two first contact regions, a second electrode region and a second contact region; a graphite-based paste layer on the first electrode region array; a ruthenium dioxide sensing layer on the graphite-based paste layer and electrically connected to the first contact region; a vitamin C enzyme layer on the ruthenium dioxide sensing layer; and a reference electrode on the second electrode region electrically connected to the second contact region.

27 Claims, 7 Drawing Sheets

SEPARATIVE EXTENDED GATE FIELD EFFECT TRANSISTOR BASED VITAMIN C SENSOR AND FORMING METHOD THEREOF

CROSS REFERENCE TO RELATED APPLICATIONS

This Application claims priority of Taiwan Patent Application No. 097124536, filed on Jun. 30, 2008, the entirety of which is incorporated by reference herein.

BACKGROUND OF THE INVENTION

1. Field of the Invention

The present invention relates to a vitamin C bio-sensor, and in particular relates to a separative extended gate field effect transistor based vitamin C sensor.

2. Description of the Related Art

Vitamin C is an antioxidant related to oxidation of aromatic amino acids, and synthesis of norepinephrine. Vitamin C also plays a role of reducing the $Fe^{3+}$ ions when transferring ferritin in bodily fluids. Vitamin C is needed for hydrogenation of lysine and proline and is mainly in collage. Collagen is needed for growth of cartilage and bone. Lack of vitamin C, leads to hemorrhaging.

The ion sensitive field effect transistor (ISFET) was first invented by P. Bergveld in 1970, and the ISFET is based on a metal-oxide-semiconductor field effect transistor (MOSFET). Moreover, the gate of the MOSFET was replaced by a sensing membrane and electrolyte. A sensing membrane and $H^+$ and $OH^-$ in a sample solution results in an adsorption-binding effect to make the potential on the surface of an electrode change, thus obtaining the ion concentration of a sample solution.

If an appropriate enzyme is selected to be on the ion sensing film, concentration of different enzymes may be detected. This structure is called an enzyme field effect transistor (EnFET). The earliest report of EnFETs, used EnFETs for detecting penicillin. After that, various enzyme field effect transistor based structures were used as enzyme bio sensors.

In 1995, R. Nagata and I. Karube et al used a screen printing process to fabricate an amperometric glucose sensor. A plastic film was used as a substrate, and platinum was used as electrodes. Glucose oxidase coated with ferrocence, n-pentanol and polyvinylutyral were mixed as an ink. The ink was sprayed on the platinum electrodes and the ferrocence was used as an electron mediator to decrease the oxidation reduction potential to resist interferon of other ions. Resin was used as physical colloid immobilized substance. After the ink was dried, the ion sensing film was immobilized on the platinum electrodes.

BRIEF SUMMARY OF THE INVENTION

The invention provides a separative extended gate field effect transistor based vitamin C sensor, including: a substrate; a patterned conductive layer on the substrate, including: a first electrode region array; at least two first contact regions; a second electrode region; and a second contact region; a graphite-based paste layer on the first electrode region array; a ruthenium dioxide sensing layer on the graphite-based paste layer and electrically connected to the first contact regions; a vitamin C enzyme layer on the ruthenium dioxide sensing layer; and a reference electrode on the second electrode region electrically connected to the second contact region.

The invention provides a method for forming a separative extended gate field effect transistor based vitamin C sensor, including: (a) providing a substrate; (b) forming a patterned layer array on the substrate, wherein the patterned layer array comprises: a first electrode region array; at least two first contact regions; a second electrode region; and a second contact region; (c) forming a graphite-based paste layer on the first electrode regions; (d) forming a ruthenium dioxide sensing layer on the graphite-based paste layer, wherein the ruthenium dioxide sensing layer is electrically connected to the first contact regions; (e) forming a reference electrode on the second contact region electrically connected to the second contact region; and (f) forming a vitamin C enzyme layer on the ruthenium dioxide sensing layer, wherein the vitamin C enzyme layer comprises an ascorbic acid oxidase.

A detailed description is given in the following embodiments with reference to the accompanying drawings.

BRIEF DESCRIPTION OF THE DRAWINGS

The present invention can be more fully understood by reading the subsequent detailed description and examples with references made to the accompanying drawings, wherein.

DETAILED DESCRIPTION OF THE INVENTION

The following description is of the best-contemplated mode of carrying out the invention. This description is made for the purpose of illustrating the general principles of the invention and should not be taken in a limiting sense. The scope of the invention is best determined by reference to the appended claims.

This description will be directed in particular to elements forming part of, or cooperating more directly with, an apparatus in accordance with the present invention. It is to be understood that elements not specifically shown or described may take various forms well known to those skilled in the art.

Figure 1:
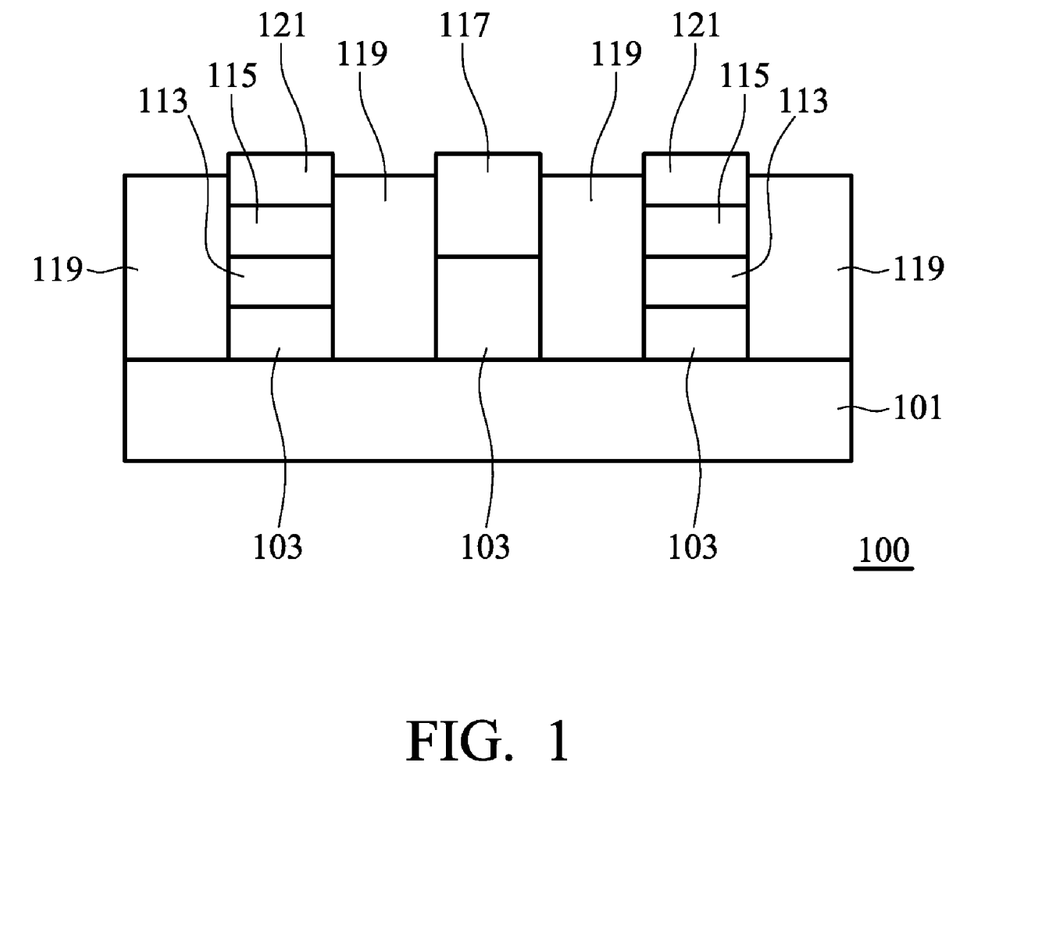
FIG. 1 illustrates a section view of a separative extended gate field effect transistor based vitamin C sensor of an embodiment of the invention.
Figure 2:
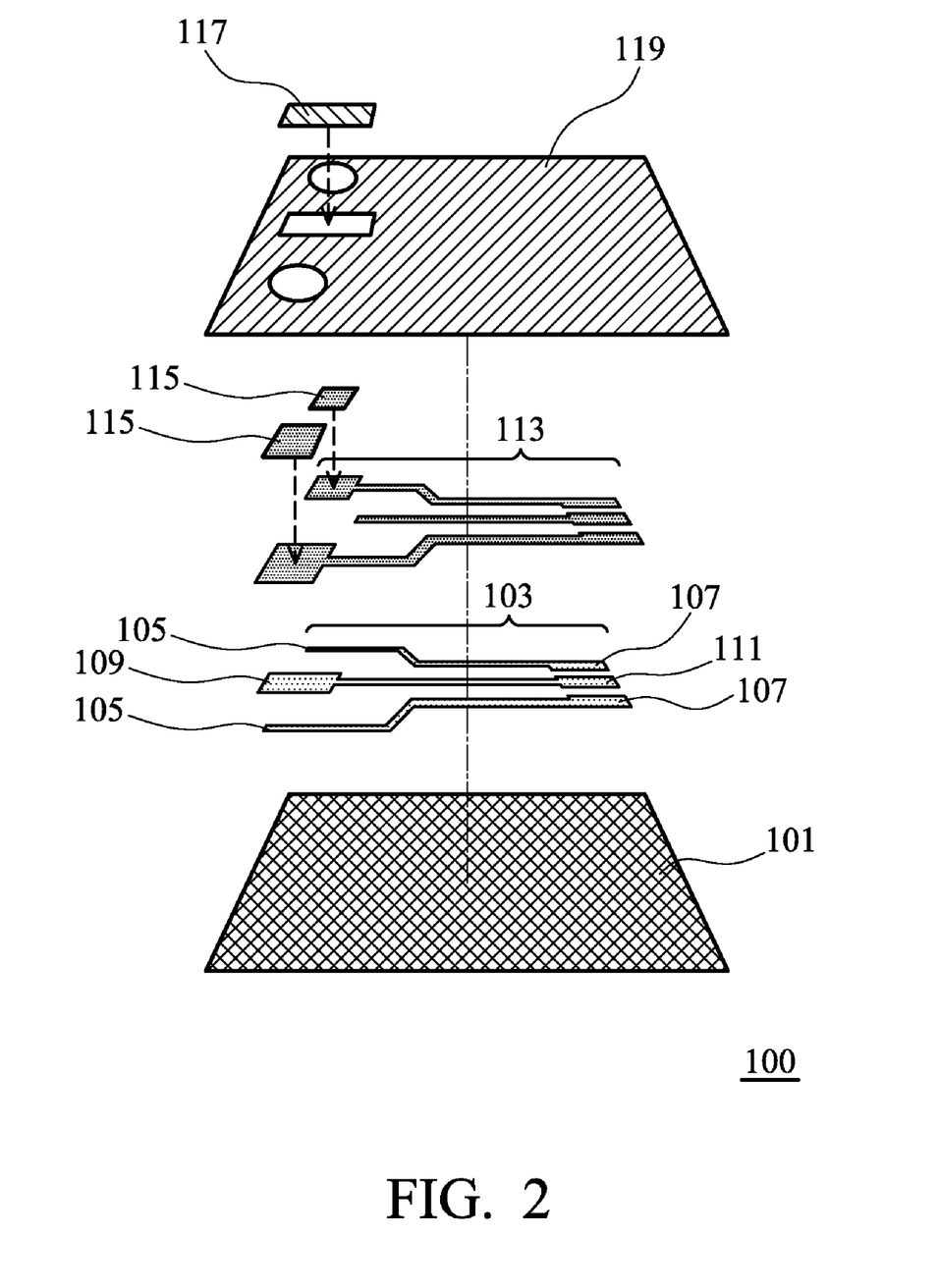
FIG. 2 illustrates a dissolution view of a separative extended gate field effect transistor based vitamin C sensor of an embodiment of the invention.

See FIG. 1 and FIG. 2. FIG. 1 illustrates a section view of a separative extended gate field effect transistor based vitamin C sensor of an embodiment of the invention. FIG. 2 illustrates a dissolution view of a separative extended gate field effect transistor based vitamin C sensor of an embodiment of the invention. A method for forming a separative extended gate field effect transistor based vitamin C sensor of the invention will be described in the following.

First, a substrate 101 is formed on a patterned conductive layer 103. The patterned conductive layer 103 may comprises a first electrode region array 105, at least two first contact regions 107, a second electrode region 109 and a second contact region 111. Preferably, the patterned conductive layer 103 is formed by a screen printing process since the screen printing process may use various printing material to perform printing. However, other traditional methods may also be used for forming the patterned conductive layer 103. The material used for forming the patterned conductive layer 103 comprises silver paste, preferably. Furthermore, the first electrode region array 105 may comprises a 1×2 array, 2×2 array, 4×4 array or larger array. In one embodiment, the first electrode region array 105 is arrayed 1×2.

Next, a graphite-based paste layer 113 is formed on the first electrode regions 105 to protect the patterned conductive layer 103 and enhance electric conduction. The graphite-based paste layer 113 may be only formed on the first electrode regions 105 or be formed extending on the entire patterned conductive layer 103 to expose the second electrode region 109.

Then, a ruthenium dioxide sensing layer 115 is formed on the graphite-based paste 113 layer on the first electrode region array 105 and electrically connected to the first contact regions 107. In one embodiment, the ruthenium dioxide sensing layer 115 is formed by a radio frequency sputtering process. A processing time for the radio frequency sputtering process is about 20-40 minutes, preferably 30 minutes. A titanium dioxide target used in the radio frequency sputtering process is with purity greater than 99.99%, preferably with purity greater than 99.99%. Power of the radio frequency sputtering process mentioned above is about 100-120 W, preferably 100 W. A processing pressure for the radio frequency sputtering process is about 10-15 mTorr, preferably 10 mTorr.

An insulation protection layer 119 may be additionally formed on the graphite-based paste layer 113 to protect the patterned conductive layer 103 and the graphite-based paste layer 113 and the forming method thereof may comprise a screen printing process. An original material of the insulation protection layer 119 may comprise a UV-cured paste. In one embodiment, the UV-cured paste is exposed under high power UV light to be curded to form an insulation protection layer of a cured form UV-cured paste. The insulation protection layer is patterned for exposing the ruthenium dioxide sensing layer 115 on the first electrode regions 105 and the second electrode region 109, and the insulation protection layer will expose a vitamin C enzyme layer 121 and a reference electrode 117 of the completed structure.

Then, the reference electrode 117 is formed on the second electrode region 109 and electrically connected to the second contact region 111. A material of the reference electrode 117 may comprise high conductive polymer. In one embodiment, the high conductive polymer is polypyrrole (PPy). A method for forming the reference electrode 117 may comprise an electro polymerization process. In one embodiment, an electro polymerization solution used in the electro polymerization process may comprise potassium phosphate ($K_2HPO_4$ and $KH_2PO_4$), KCl, acetonitrile ($CH_3CN$) and pyrrole ($C_4H_5N$) and the concentration of each is 0.05-0.5 M, 0.1-0.3 M, 0.5-3 M and 0.1-0.5 M, respectively, and preferably, 0.1 M, 0.1 M, 1 M and 0.3 M, respectively.

Finally, the vitamin C enzyme layer 121 is formed on the ruthenium dioxide sensing layer 115 to complete the enzyme sensor 100 of the invention, wherein the vitamin C enzyme layer 121 may comprise an ascorbic acid oxidase. The vitamin C enzyme layer 121 may be formed by a covalent bonding process using enzyme immobilization technology.

Enzyme immobilization means that an enzyme is attached to or included in an unsoluble solid support (so called carrier), or that enzymes are connected to each other without damaging the activity thereof. In one embodiment, a covalent bonding process is used for enzyme immobilization and the carriers needed in the process may be a 3-glycidoxypropyltrimethoxysilane (GPTS) solution and toluene. A volume ratio of the 3-glycidoxypropyltrimethoxysilane (GPTS) solution to toluene may be about 0.5-2:8.5-10, preferably about 1:9.

After the separative extended gate field effect transistor based vitamin C sensor of the invention is completed, the larger the first electrode region array is, the more regions are available to detect vitamin C. For example, when the first electrode region array 105 is arrayed 2×2, there will be four regions which are able to detect vitamin C. The region which is able to detect vitamin C, can also be called the sensing window, and thus when the first electrode region array 105 is arrayed 2×2, there will be four sensing windows.

Moreover, the sensitivity of the separative extended gate field effect transistor based vitamin C sensor of the invention is about 18-25 mV/mM, preferably 22.24 and the linearity of the separative extended gate field effect transistor based vitamin C sensor of the invention is about 0.90-0.99, preferably 0.987.

EXAMPLE

Preparation of the Vitamin C Sensors

1. Procedure of the Vitamin C Sensor Preparation

The design and preparation procedure of the vitamin C sensor are shown in the following:

(1) A 20 μm thick silver paste was deposited on a PET substrate by a screen printing machine and then was placed in a 100° C. oven, for, 15 minutes to be cured.

(2) A 20 μm thick graphite-based paste layer was deposited and then was placed in a 100° C. oven, for, 15 minutes to be cured.

(3) A ruthenium dioxide sensing layer was deposited on the graphite-based paste 113 by a screen-printing process.

(4) A 50 μm thick UV-cured paste was deposited and sensing windows of 1.5 mm in diameter were preserved. The 50 μm thick UV-cured paste was exposed under UV light for 40 seconds to be cured to protect the device.

(5) A reference electrode was prepared.

(6) Vitamin C enzymes were immobilized.

2. Preparation of the Silver Paste, Graphite-Based Paste and UV-Cured Paste (1) A semi-automatic screen printing machine (HJ-55AD3, Houn Jien Co., Ltd.) was checked for proper operation and a gas valve thereof was opened to let the processing air pressure reach 5-6 $Kg/cm^2$.

(2) A gas inhaling switch was switched on (to prevent the substrate and the ink to adhere to each other).

(3) An amount for screen printing was set.

(4) A model of screen-printing was set.

(5) The silver paste, graphite-based paste and UV-cured paste was formed through the method mentioned above.

3. Preparation of the Ruthenium Dioxide Sensing Layer

The ruthenium target used in the example was 2 inches in diameter, 3 mm in thickness and with purity of 99.99%. Argon and oxygen were from San Feng Chemical Co., Ltd.

During the sputtering processing, the device and the target were placed in a chamber, and a shutter was used to cover the device. A rotary pump was used to let the vacuum reach 5 mTorr and then a turbo pump was used to let the vacuum in the chamber reach below $5\times10^{-6}$ mTorr.

Argon and oxygen of different ratios were introduced into the chamber to modulate the processing and the flow rates of the gases were controlled by a mass flow controller.

During the processing procedure, the power of the radio frequency sputtering process was 100 W and when argon and oxygen with different ratios were introduced into the chamber, the pressure for radio frequency sputtering process was 10 mTorr. An RF power generator was switched on to produce plasma, and RF power and the pressure for the radio frequency sputtering process were modulated according to required conditions. 15 minutes of pre-sputtering was performed to clean out impurities, such as an oxide layer formed from contact with air on the surface of the target. After the plasma was stable, the shutter was removed to perform the sputtering process for 15 minutes to form the ruthenium dioxide film. During the sputtering process, a condensation system was used to maintain the low temperature.

When the sputtering process was finished, the piping for gas flowing in the chamber was closed. A rotary pump was used to pump the un-reacted gas out and after 30 minutes the prepared ruthenium dioxide film was moved out the chamber while the condensation system was used to decrease the temperature in the chamber to reduce the oxidation of the ruthenium dioxide film and the target before the vacuum was broken.

4. Preparation of the Miniaturized Reference Electrode (1) 0.1 M KCl, 1 M acetonitrile, 0.3 M pyrrole ($C_4H_5N$) and 0.1 M PBS buffer were mixed for 3-5 minutes to form an electro polymerization solution.

(2) A positive electrode and negative electrode of a DC power supply (adjust to 2.5 V) were connected to the second electrode region of the sensor device of the invention and a platinum electrode, respectively.

(3) The second electrode region of the sensor device was dipped into the electro polymerization solution for 30 minutes to form a miniaturized reference electrode.

(4) After the electro polymerization process was finished, the miniaturized reference electrode was dipped in D.I. water for 30 minutes to remove the un-polymerized high conductive polymers.

(5) The miniaturized reference electrode was remove from D.I. water and dried for 12 hours.

(6) The miniaturized reference electrode was dipped into a 6 M NaOH solution for 30 seconds.

(7) The miniaturized reference electrode was remove from the 6 M NaOH solution and dipped in D.I. water for 30 minutes. The miniaturized reference electrode was remove from D.I. water and dried to complete the preparation of the miniaturized reference electrode.

5. Immobilization of the Vitamin C Enzyme (1) The sensing windows were washed with D.I. water.

(2) 3-glycidoxypropyltrimethoxysilane and toluene mixture (volume ratio: 1:9) was dropped on the sensing windows and then placed in a 80° C. oven for 1 hour.

(3) The sensing windows were cooled, and then were dipped in a PBS buffer for 10 minutes to wash out the remaining 3-glycidoxypropyltrimethoxysilane and toluene mixture.

(4) Ascorbic acid oxidase solution was prepared (1 mg of ascorbic acid oxidase was dissolved in 1 ml of PBS buffer) and then a 10 μl of ascorbic acid oxidase solution was dropped on the sensing windows and then was placed in a refrigerator for 12 hours.

(5) An appropriate amount of cooled PBS buffer was used to wash out the un-immobilized ascorbic acid oxidase to complete the immobilization of the vitamin C enzyme.

Preparation of Sample Solutions

1. Preparation of the Buffer (1) 3.4023 g of $KH_2PO_4$ (MW:136.09) and 500 ml of D.I. water were mixed to obtain a 50 mM $KH_2PO_4$ buffer (pH 4.6).

(2) 4.3545 g of $K_2HPO_4$ (MW:174.18) and 500 ml of D.I. water were mixed to obtain a 50 mM $KH_2PO_4$ buffer (pH 8.8).

(3) 230 ml of the $KH_2PO_4$ buffer was added into 400 ml of $KH_2PO_4$ buffer and adjusted to pH 7.2 to obtain a PBS buffer (50 mM, pH 7.2). The PBS buffer was used to prepare the vitamin C sample solutions.

2. Preparation of the Vitamin C Sample Solutions (1) A 2 mM vitamin C sample solution was prepared. 0.0352 g of vitamin C was added into 100 ml of PBS buffer (50 mM, pH 7.2) and then well mixed.

(2) 50 ml of 2 mM vitamin C sample solution was added into 100 ml of PBS buffer to obtain a 100 ml of 1 mM vitamin C sample solution.

(3) The method mentioned previously was used to dilute 1 mM, 0.5 mM, 0.25 mM and 0.0125 mM vitamin C sample solutions, to obtain 0.5 mM, 0.25 mM and 0.0125 mM and 0.00625 mM vitamin C sample solution, respectively.

Measuring System

Voltage-Time (V-T) Measuring System

Figure 3:
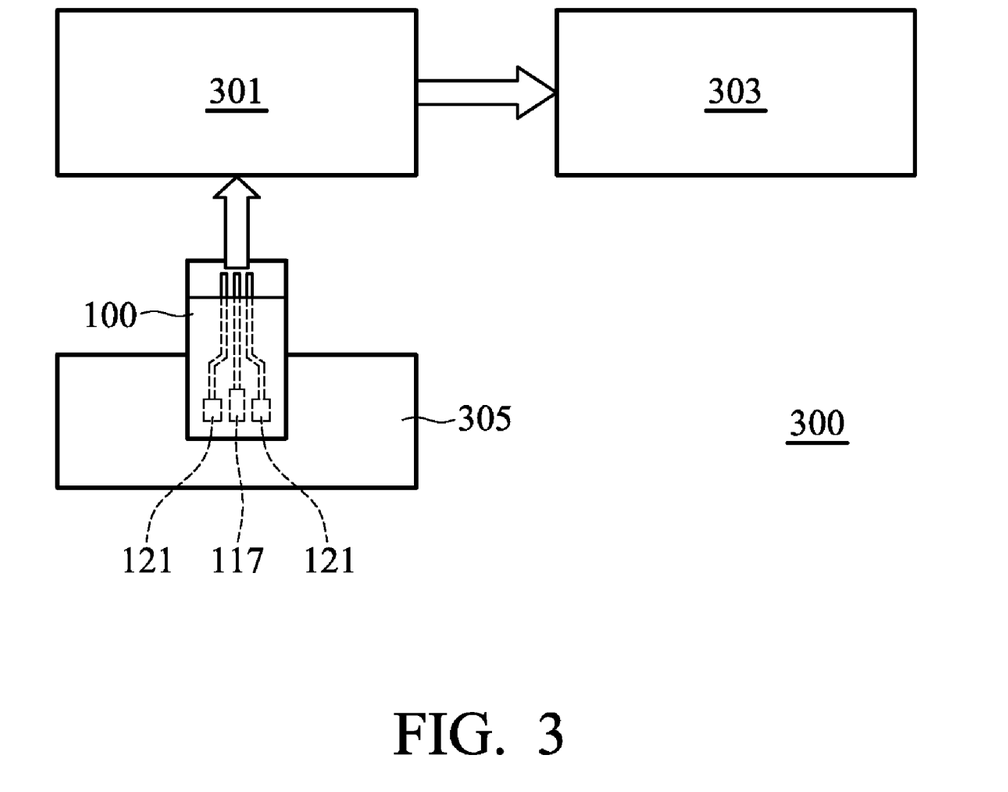
FIG. 3 shows a vitamin sample solution measured by a V-T measuring system combined with the separative extended gate field effect transistor based vitamin C sensor of the invention.

See FIG. 3. The Voltage-Time (V-T) measuring system 300 used in the invention is shown in FIG. 3. The data acquisition (USB-6008 and PCI-6010 DAQ) 301 was connected first to the contact regions 107 comprising the vitamin C enzyme layer 121, and reference electrode 117, wherein the data acquisition 301 included eight-channel signal importation, and data acquisition 301 signals were recorded by the computer 303. Afterwards, the LabVIEW 7.1 (National Instruments Incorporation) was used to record the signals, and then the Origin 7.0 (OriginLab Corporation) was used to analyze the signals.

Method for Data Fusion Analysis

Standard deviation measures the spread of a collection of numbers about a mean value. A large standard deviation value means that most of the collection of numbers is far from the mean thereof and a small standard deviation value means that most of the collection of numbers is closer to the mean thereof.

If the collection of numbers is hypothesized to be $x_1, \ldots, x_N$ (all are real numbers), then the mean of the collection of numbers will be:

$$\bar{x} = \frac{1}{N} \sum_{i=1}^{N} x_i,$$

wherein the standard deviation of the collection of numbers will be:

$$\sigma = \sqrt{\frac{1}{N-1} \sum_{i=1}^{N} (x_i - \bar{x})^2}. \tag{1}$$

If the condition of m sensors directly measure a one dimension, the measuring equation may be hypothesized to be:

$$z_i(k) = x(k) + v_i(k) \quad k=1, 2, \ldots, n \; i=1, 2, \ldots, m,$$

wherein n is the magnitude of the signal, m is the mount of the sensors, $z_i(k) \in R^1$ is the measurement value of sensor measuring the target at time k, $x(k) \in R^1$ is the target condition which will be estimated and $v_i(k) \in R^1$ is the measurement value of sensor measuring the target at time k. When information is lacking, and only x can be confirmed through the measurement value, the best estimated value $\hat{x}$ is the linear weighted average of the observational values. When there are two sensors, i.e. $\hat{x} = k_1 z_1 + k_2 z_2$, that means the best estimated value was obtained at minimum. An unbiased estimator x was simplified so that an estimated mean squared error may be calculated to be a minimum.

Estimated error:

$$\tilde{x} = x - \hat{x} = x - (k_1 z_1 + k_2 z_2) \quad (2).$$

Estimated unbiased requirements:

$$E(\tilde{x}) = E[x - k_1(x+v_1) - k_2(x+v_2)] = 0 \quad (3),$$

and $$k_1 + k_2 = 1 \quad (4).$$

Since, $v_1$ and $v_2$ are independent, the estimated mean squared error will be:

$$E(\tilde{x}^2) = E\{[x - k_1(x+v_1) - k_2(x+v_2)]^2\} = k_1^2 \sigma_1^2 + (1-k_1)^2 \sigma_2^2 \quad (5)$$

At a minimum mean squared error, if it is desired to obtain the best estimate of the target signal, only k1 be appropriately chosen to let the equation (5) be a minimum and the partial derivatives related to k1 would be calculated, so that the partial derivatives commanded as 0 may be obtained such as:

$$k_1 = \sigma_2^2/(\sigma_1^2 + \sigma_2^2), k_2 = \sigma_1^2/(\sigma_1^2 + \sigma_2^2) \quad (6).$$

Therefore, the best estimate of the signal x is:

$$\hat{x} = k_1 z_1 + k_2 z_2 \quad (7).$$

The weighted factors $k_1$ and $k_2$ may be obtained from the equation (6). The equation (7) shows that the smaller the mean squared error is, the more reliable the measurement value is and the larger the corresponding weighted factors are. On the other hand, the larger the mean squared error is, the less reliable the measurement value is and the smaller the corresponding weighted factors are.

Mean-squared error of estimated error:

$$\hat{\sigma}^2 \equiv E(\tilde{x}^2) = k_1^2 \sigma_1^2 + k_2^2 \sigma_2^2 = (\sigma_1^{-2} + \sigma_2^{-2})^{-1} \quad (8).$$

The equation (8) shows that $\hat{\sigma}^2 < \sigma_i^2$ and i=1, 2, i.e. at a minimum mean squared error. After the data of two sensors is fused, the estimated effect of the two sensors is better than the estimated effect of one sensor and the fusion may idealize the sensing windows at a worse condition. A method for data fusion analysis may be used for a larger array of the sensor mentioned in the invention to increase the accuracy of the sensor.

Sensing of H+ Ion

Figure 4:
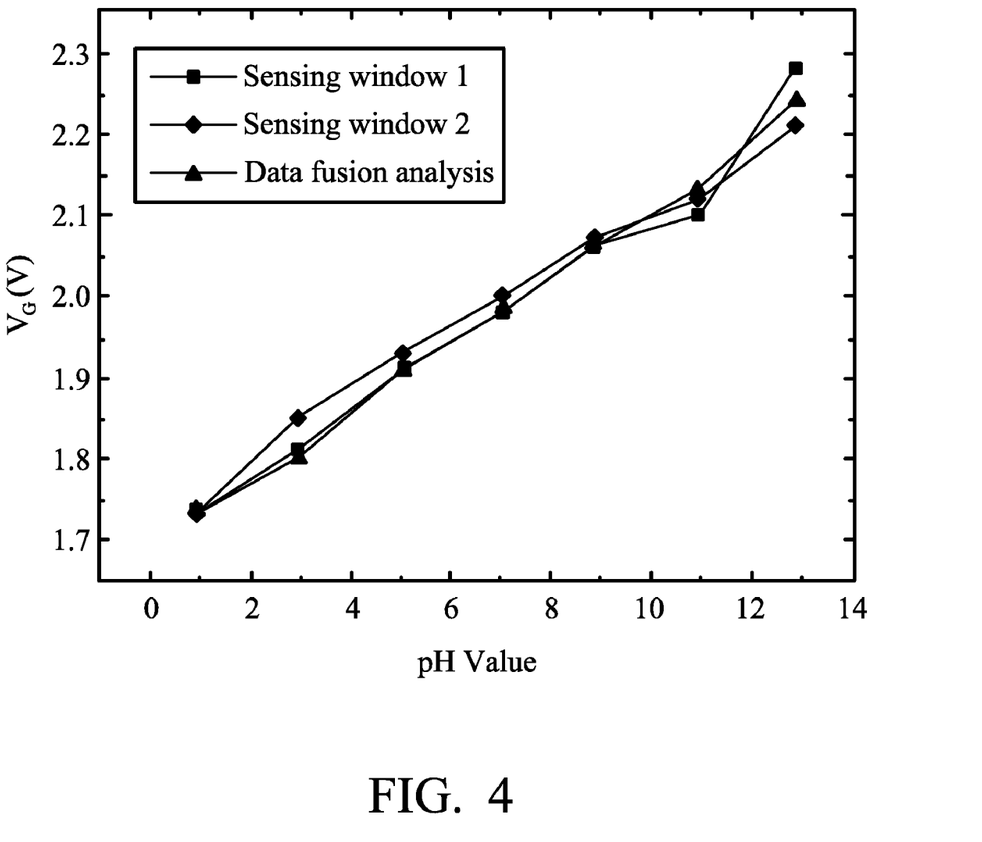
FIG. 4 shows a first measurement result, with response voltage of different concentrated solutions being obtained through data fusion analysis.
Figure 5:
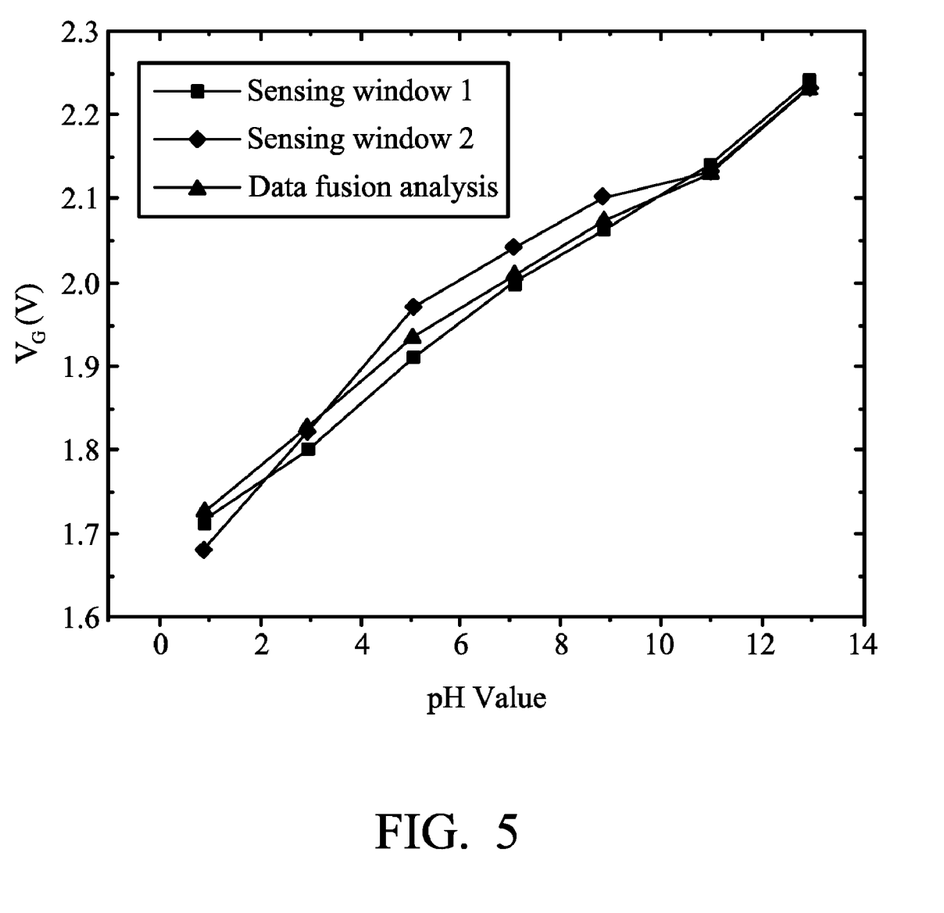
FIG. 5 shows a second measurement result, with response voltage of different concentrated solutions being obtained through data fusion analysis.

H+ ion sensing is an important factor to determine the performance of a sensor. During the test, a vitamin C sensor with 1×2 sensing windows of the invention was dipped into an acid/base solution to let the sensing windows and the reference electrode result in an output voltage. Voltage analysis obtained from the acid/base solutions with different concentrations was used to obtain sensitivity and linearity of the sensor. A first test result of a vitamin C sensor with 1×2 sensing windows of the invention is shown in FIG. 4. The sensitivities of the two sensing windows are 38.1 mV/pH and 43.2 mV/pH, respectively and the linearity of the two sensing windows are 0.994 and 0.976, respectively. Data fusion analysis was performed on the measuring data of the two sensing windows to obtain the sensitivity and linearity of the sensor which were 40.5 mV/pH and 0.995, respectively. Moreover, the sensing range in the test mentioned above was pH 1-pH13. A second test result of a vitamin C sensor with 1×2 sensing windows of the invention is shown as FIG. 5.

The data fusion analysis is shown in the following:

n: Measurement of $n^{th}$ time;

$\sigma_n^2$: Variance error;

$k_n$: Weighted factor;

n': Measurement of $n^{th}$ time by data fusion analysis.

The data fusion analysis result of a sensor being immersed in pH1 solution is shown in the following:

The equation (1) mentioned above showed that:

Sensing Window 1:

Mean $\bar{x} = (1.74 + 1.73)/2 = 1.735$ $$\sigma_1^2 = \frac{1}{N-1} \sum_{i=1}^{N} (x_i - \bar{x})^2 = \frac{1}{2-1}[(1.74 - 1.735)^2 + (1.73 - 1.735)^2] = 0.00005;$$

and

Sensing Window 2:

Mean $\bar{x} = (1.71 + 1.68)/2 = 1.695$ $$\sigma_2^2 = \frac{1}{2-1}[(1.71 - 1.695)^2 + (1.68 - 1.695)^2] = 0.00045.$$

From the equation (6), the weighted factors may be obtained as:

$$k_1 = \sigma_2^2/(\sigma_1^2 + \sigma_2^2) = (0.00045)/(0.00005 + 0.00045) = 0.9,$$

and $$k_2 = \sigma_1^2/(\sigma_1^2 + \sigma_2^2) = (0.00005)/(0.00005 + 0.00045) = 0.1.$$

Then, through the equation (7), the data fusion analysis result could be obtained as follows.

The data fusion analysis result of the first test result = $k_1 z_1 + k_2 z_2 = 0.9 \times 1.74 + 0.1 \times 1.71 = 1.737$.

The data fusion analysis result of the second test result = $k_1 z_1 + k_2 z_2 = 0.9 \times 1.73 + 0.1 \times 1.68 = 1.725$.

TABLE 1

| | The data fusion analysis results of the first and second test results | | | | | | | |
|---|---|---|---|---|---|---|---|---|
| pH value | n = 1 | n = 2 | $\sigma_1^2$ | $\sigma_2^2$ | $k_1$ | $k_2$ | n' = 1 | n' = 2 |
| 1 | 1.74 | 1.73 | 0.00005 | 0.00045 | 0.9 | 0.1 | 1.737 | 1.725 |
| | 1.71 | 1.68 | | | | | | |
| 3 | 1.81 | 1.85 | 0.0008 | 0.0002 | 0.2 | 0.8 | 1.802 | 1.826 |
| | 1.8 | 1.82 | | | | | | |

TABLE 1-continued

The data fusion analysis results of the first and second test results

| pH value | n = 1 | n = 2 | $\sigma_1^2$ | $\sigma_2^2$ | $k_1$ | $k_2$ | n' = 1 | n' = 2 |
|---|---|---|---|---|---|---|---|---|
| 5 | 1.91 | 1.93 | 0.0002 | 0.0018 | 0.9 | 0.1 | 1.91 | 1.934 |
|   | 1.91 | 1.97 |  |  |  |  |  |  |
| 7 | 1.98 | 2.0 | 0.0002 | 0.0008 | 0.8 | 0.2 | 1.984 | 2.008 |
|   | 2.0 | 2.04 |  |  |  |  |  |  |
| 9 | 2.06 | 2.07 | 0.00005 | 0.0008 | 0.941176 | 0.058824 | 2.06 | 2.071765 |
|   | 2.06 | 2.1 |  |  |  |  |  |  |
| 11 | 2.1 | 2.12 | 0.0002 | 0.00005 | 0.2 | 0.8 | 2.132 | 2.128 |
|    | 2.14 | 2.13 |  |  |  |  |  |  |
| 13 | 2.28 | 2.21 | 0.00245 | 0.00005 | 0.02 | 0.98 | 2.2408 | 2.2296 |
|    | 2.24 | 2.23 |  |  |  |  |  |  |

The data shown in Table 1 through Origin 7.0 (OriginLab Corporation) obtained sensitivity and the linearity data of each sensing window before and after data fusion analysis and the data is shown in Table 2.

TABLE 2

Sensitivity and the linearity data of each sensing window before and after data fusion analysis

|  |  | Sensitivity | Linear regression |
|---|---|---|---|
| First measurement | Sensing window 1 | 42.2 | 0.987 |
|  | Sensing window 2 | 43.5 | 0.998 |
|  | Data fusion analysis | 41.7 | 0.998 |
| Second measurement | Sensing window 1 | 38.1 | 0.994 |
|  | Sensing window 2 | 43.2 | 0.976 |
|  | Data fusion analysis | 40.5 | 0.995 |

Selection for Concentration of a Buffer

Figure 6:
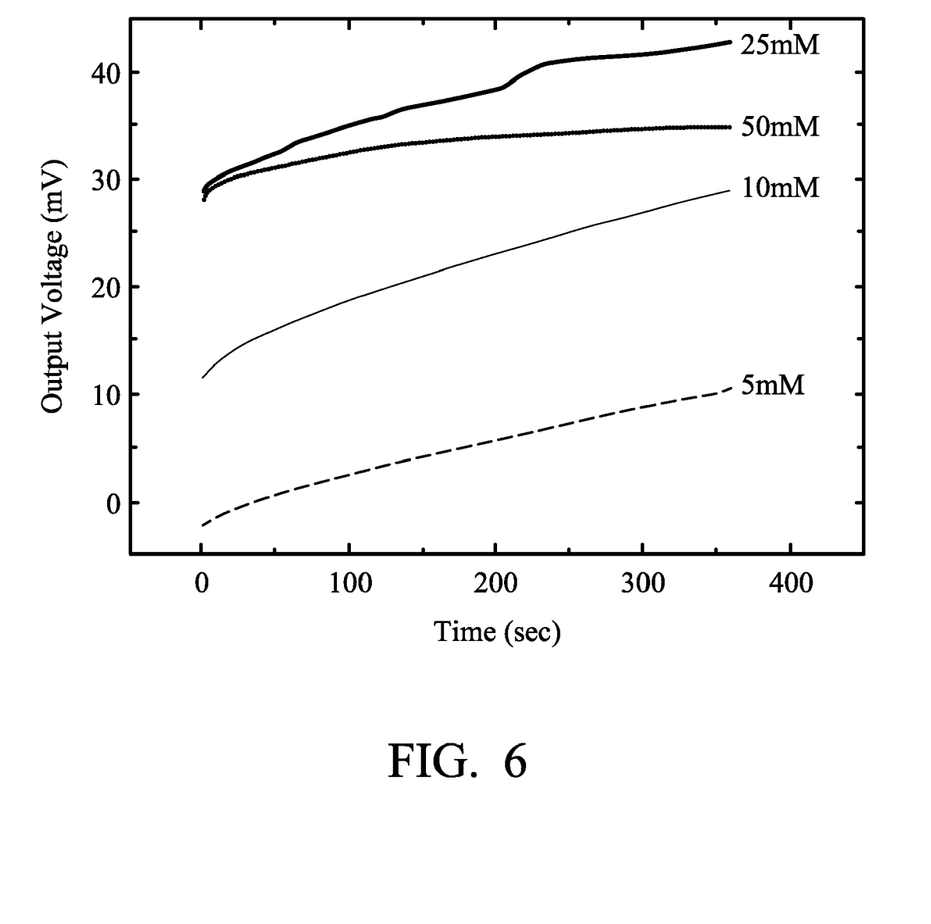
FIG. 6 shows time-voltage curves of 0.25 mM vitamin C in different phosphate buffer solutions (PBS).

When a small amount of H$^+$ or OH$^-$ ions is increased in a buffer, the buffer is capable of resisting change of the pH value. The higher the concentration is, the more stable the pH value of the buffer is. The lower the concentration is, the less stable the pH value of the buffer is. The selection result is shown in FIG. 6. 50 mM PBS was used for the sensor of the present invention and the sensor had good stability in the buffer.

Sensing for Vitamin C 1 ml of buffer (50 mM, pH7.0) and 1 mg of ascorbic acid oxidase were mixed to prepare an ascorbic acid oxidase solution. According the manual of the commercial ascorbic acid oxidase, there were 1000-3000 units of ascorbic acid oxidase per mg, and thus 1 μl of the ascorbic acid oxidase solution had 1-3 units of ascorbic acid oxidase. During immobilization of the enzyme, 10 μl of the ascorbic acid oxidase solution was dropped on the sensing window. Furthermore, according the manual of the commercial ascorbic acid oxidase, 1-3 units of ascorbic acid oxidase can react with 1.0μ mole of vitamin C per minute, and thus 0.25 mM of vitamin C needed a time of 60-200 seconds to be stable.

Figure 7:
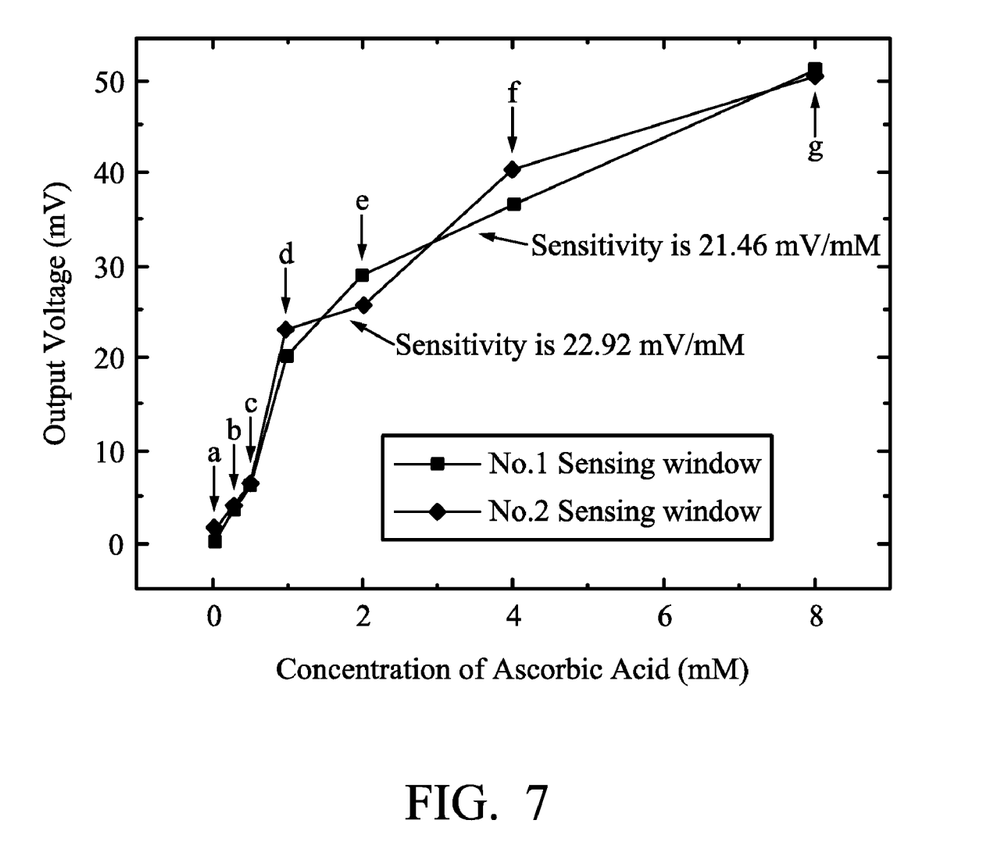
FIG. 7 shows measurement of the vitamin C array sensors in the following concentrated solutions: (a) 0.06 mM; (b) 0.25 mM; (c) 0.5 mM; (d) 1 mM; (e) 2 mM; (f) 4 mM; (g) 8 mM.

FIG. 3 shows a vitamin sample solution 305 measured by a V-T measuring system combined with the separative extended gate field effect transistor based vitamin C sensor of the invention. According the measuring results as show in FIG. 7, the sensitivity of the sensor was 21.46 mV/mM and 22.92 mV/mM, and after data fusion analysis, the sensitivity of the sensor was 22.24 mV/mM, and linearity range of the sensor was 0.06-1 mM.

While the invention has been described by way of example and in terms of the preferred embodiments, it is to be understood that the invention is not limited to the disclosed embodiments. To the contrary, it is intended to cover various modifications and similar arrangements (as would be apparent to those skilled in the art). Therefore, the scope of the appended claims should be accorded the broadest interpretation so as to encompass all such modifications and similar arrangements.

What is claimed is:

1. A separative extended gate field effect transistor based vitamin C sensor, comprising:
    a substrate;
    a patterned conductive layer on the substrate, comprising:
        a first electrode region array;
        at least two first contact regions;
        a second electrode region; and
        a second contact region;
    a graphite-based paste layer on the first electrode region array;
    a ruthenium dioxide sensing layer on the graphite-based paste layer and electrically connected to the first contact regions;
    a vitamin C enzyme layer on the ruthenium dioxide sensing layer; and
    a reference electrode on the second electrode region electrically connected to the second contact region.

2. The separative extended gate field effect transistor based vitamin C sensor as claimed in claim 1, wherein the first electrode region array is arrayed 1×2.

3. The separative extended gate field effect transistor based vitamin C sensor as claimed in claim 1, wherein the first electrode region array is arrayed 2×2.

4. The separative extended gate field effect transistor based vitamin C sensor as claimed in claim 1, wherein the first electrode region array is arrayed 4×4.

5. The separative extended gate field effect transistor based vitamin C sensor as claimed in claim 1, wherein the substrate comprises a flexible substrate.

6. The separative extended gate field effect transistor based vitamin C sensor as claimed in claim 1, wherein the substrate comprises a polyethylene terephthalate (PET) substrate.

7. The separative extended gate field effect transistor based vitamin C sensor as claimed in claim 1, wherein a material of the patterned conductive layer comprises silver paste.

8. The separative extended gate field effect transistor based vitamin C sensor as claimed in claim 1, wherein the reference electrode comprises a high conductive polymer.

9. The separative extended gate field effect transistor based vitamin C sensor as claimed in claim 1, further comprising an insulation protection layer on the graphite-based paste layer exposing the vitamin C enzyme layer on the ruthenium dioxide sensing layer and the reference electrode.

10. The separative extended gate field effect transistor based vitamin C sensor as claimed in claim 9, wherein an original material of the insulation protection layer is a UV-cured paste.

11. The separative extended gate field effect transistor based vitamin C sensor as claimed in claim 1, wherein a sensitivity of the separative extended gate field effect transistor based vitamin C sensor is about 18-25 mV/mM.

12. A method for forming a separative extended gate field effect transistor based vitamin C sensor, comprising:
(a) providing a substrate;
(b) forming a patterned layer array on the substrate, wherein the patterned layer array comprises:
a first electrode region array;
at least two first contact regions;
a second electrode region; and
a second contact region;
(c) forming a graphite-based paste layer on the first electrode regions;
(d) forming a ruthenium dioxide sensing layer on the graphite-based paste layer, wherein the ruthenium dioxide sensing layer is electrically connected to the first contact regions;
(e) forming a reference electrode on the second contact region electrically connected to the second contact region; and
(f) forming a vitamin C enzyme layer on the ruthenium dioxide sensing layer, wherein the vitamin C enzyme layer comprises an ascorbic acid oxidase.

13. The method as claimed in claim 12, wherein the first electrode region array is arrayed 1×2.

14. The method as claimed in claim 12, wherein the first electrode region array is arrayed 2×2.

15. The method as claimed in claim 12, wherein the first electrode region array is arrayed 4×4.

16. The method as claimed in claim 12, wherein the substrate comprises a polyethylene terephthalate (PET) substrate.

17. The method as claimed in claim 12, wherein in the step (b), the method for forming the patterned layer array comprises a screen printing process.

18. The method as claimed in claim 12, wherein a material of the patterned conductive layer comprises silver paste.

19. The method as claimed in claim 12, wherein in the step (c), the method for forming the graphite-based paste layer comprises a screen printing process.

20. The method as claimed in claim 12, wherein in the step (d), the method for forming the ruthenium dioxide sensing layer comprises a radio frequency sputtering process.

21. The method as claimed in claim 12, wherein in the step (e), the method for forming the reference electrode comprises an electro polymerization process.

22. The method as claimed in claim 21, wherein an electro polymerization solution used in the electro polymerization process comprises potassium phosphate ($K_2HPO_4$ and $KH_2PO_4$), KCl, acetonitrile ($CH_3CN$) and pyrrole ($C_4H_5N$).

23. The method as claimed in claim 22, wherein the potassium phosphate ($K_2HPO_4$ and $KH_2PO_4$) is 0.05-0.5 M, KCl is 0.1-0.3 M, acetonitrile ($CH_3CN$) is 0.5-3 M and pyrrole ($C_4H_5N$) is 0.1-0.5 M.

24. The method as claimed in claim 12, wherein in the step (f), the method for forming the vitamin C enzyme layer comprises a covalent bonding process using enzyme immobilization technology.

25. The method as claimed in claim 24, wherein a carrier used in the covalent bonding process comprises a 3-glycidoxypropyltrimethoxysilane (GPTS) solution and toluene.

26. The method as claimed in claim 12, after the step (d), further comprising forming an insulation protection layer on the graphite-based paste layer exposing the vitamin C enzyme layer on the ruthenium dioxide sensing layer and the reference electrode.

27. The method as claimed in claim 26, wherein an original material of the insulation protection layer is a UV-cured paste.

* * * * *